United States Patent [19]

Lindberg

[11] Patent Number: Plant 7,461

[45] Date of Patent: Mar. 5, 1991

[54] MINIATURE ROSE PLANT NAMED RUIKULI

[75] Inventor: Kurt Lindberg, Akarp, Sweden

[73] Assignee: DeRuiter's Nieuwe Rozen B.V., Netherlands

[21] Appl. No.: 410,540

[22] Filed: Sep. 21, 1989

[51] Int. Cl.[5] ..... A01H 5/00

[52] U.S. Cl. ..... Plt./10

[58] Field of Search ..... Plt./7, 10

[56] References Cited

U.S. PATENT DOCUMENTS

P.P. 5,976 5/1987 de Ruiter ..... Plt. 10

*Primary Examiner*—Howard J. Locker

*Attorney, Agent, or Firm*—Christie, Parker & Hale

[57] ABSTRACT

A new variety of miniature rose having red flowers produced on a good pot forcing plant also suitable for growing outdoor in gardens.

1 Drawing Sheet

SUMMARY OF THE INVENTION

The present invention relates to a new and distinct variety of rose plant of the miniature rose class, which was discovered by me as a natural mutataion in a controlled planting of the rose known as "Ruiredro", U.S. Pat. No. 5,976, the disclosure of which is incorporated herein by reference, and from which it differs in flower color. The variety denomination of this new rose is "Ruikuli".

Among the novel characteristics possessed by this new variety which distinguishes it from its parent and all other varieties of which I am aware are its red flowers borne on a plant particularly suited for production of flowering pot plants and growing in outdoor gardens and that can also be reproduced through propagation by cuttings, grafting and budding. Flowers of the new variety are long lasting on the plant. Asexual reproduction by budding, grafting and cuttings, of the new variety as performed in Åkarp, Sweden, shows that the foregoing and other distinguishing characteristics come true to form and are established and transmitted through succeeding propagation.

The accompanying drawing shows typical specimens of the vegetative growth and flowers of the new variety in different stages of development and depicted in color as nearly true as it is reasonably possible to make the same in a color illustration of this character.

BRIEF DESCRIPTION OF THE DRAWING

The photo illustration shows details of the new miniature rose variety.

DESCRIPTION OF PREFERRED EMBODIMENT

The following is a detailed description of my new variety, with color terminology in accordance with the Royal Horticultural Society Colour Chart (R.H.S.C.C.) and horticultural terminology in accordance with standard terminology used in UPOV-approved horticultural guidelies. The terminology used in color description herein refers to plate numbers in the aforementioned color chart.

Parentage: Mutation of "Ruiredro".
Class: Miniature.

The illustration shows details of the new variety "Ruikuli". In the illustration there is shown the top of young shoot, 1; compound three, five and seven leaflet leaves, 2, 3, and 4, respectively; a stem 5; a flower bud, 6 barely showing color; a flower bud, 7, after sepals separate; a flower 8 about one-third to one-half open; and a flower, 9, fully open. Also shown are flower stems, 10, 11, and 12, with reproductive organs.

The following further horticultural observations were made of specimens grown outdoor in Holland.

FLOWER

Blooming habit: Nearly continuous, very floriferous.

A. Bud:

(1) *Size.*—Medium.

(2) *Form.*—Pointed, ovate (before separation of sepals).

(3) *Color.*—As sepals divide, bud color is near 46A to 53A.

(4) *Sepal.*—Longer than bud, simple to foliated.

(5) *Penduncle.*—Length — about 4 to 5 cm. Aspect — straight. Strength — erect. Color — medium green.

B. Bloom:

*Flower.*—Average size for miniature; viewed from top — round; viewed from side (A) upper part of fully opened flower — flat; (B) lower part of fully opened flower — convex.

(1) *Size.*—Average size when fully expanded — about 4 to 5 cm.

(2) *Borne.*—Singly, one to a stem and small clusters.

(3) *Form.*—Ovoid to cupped at first, becoming flat; outer petals reflex to points; inner petals roll under slightly.

(4) *Petalage.*—Number of petals under normal conditions — about 24 to 30, fully double.

(5) *Color.*—After sepals just separate, visible petal undersurface is near 53A; when sepals part and petals begin to unfurl, predominant color is near 53A, B to 45A; viewing petal's top surface in ⅓ to ½ open stage, color surface is near 45A, B to 53B. Color through this range is substantially stable. Petal top and reverse are of similar coloring but some darkening of outer petals may open on aging. Coloring at point of petal attachment is near 2C to 2D. Overall tonality from a distance is an attractive red.

C. Petals:
(1) *Texture.*—Medium to thick.
(2) *Apperance.*—Inside velvety and outside satiny.
(3) *Form.*—Obovate.
(4) *Arrangement.*—Regularly arranged, imbricated.
(5) *Petaloids in center.*—Few.
(6) *Persistence.*—Drop off cleanly.
(7) *Fragrance.*—Slight to none.
(8) *Lasting quality.*—Very long lasting quality on plant.

REPRODUCTIVE ORGANS

A. Stamens, filaments and anthers:
*Arrangement and color.*—Regularly arranged around styles; color — filaments yellow-green.
B. Pollen: Color — yellow.
C. Styles: Even, long, stigma well above mouth of receptacle, yellow-green, upper half little to no hair, bunched.
D. Stigma: Full, extend above anthers.
E. Hips: Medium, pitcher-shaped.

PLANT

A. Form: Bushy.
B. Growth: Vigorous; height attained — about 20 to 30 cm.
C. Foliage: Compound 3, 5 and 7 leaflets.
(1) *Size.*—Medium for a miniature.
(2) *Quantity.*—Abundant.
(3) *Color.*—Foliage at time of first flowering — medium green.
(4) *Shape.*—Oval, pointed.
(5) *Texture.*—Upper side is weakly glossy; under side is matte.
(6) *Edge.*—Serrate.
(7) Serration.—Ordinary, acuminate apices.
(8) Leaf stem.—Color — medium green.
(9) Stipules.—Medium length, slightly bearded, medium to light green, distinct auricle.
(10) Leaflet.—Cross section — concave. Terminal leaflet — very short to short, narrow, obtuse base; petiole — short.

Wood:
(1) *New wood.*—Color — bronze, purple.
(2) *Old wood.*—Color — medium green.

Prickles (thorns):
(1) Prickles.—Present, quantity (main stalk) — ordinary; on laterals from stalk — few; form — straight and slanted slightly downward; shape of upper side — concave; shape of lower side — concave; length — few $\leqq 5$ mm; few $>5$ mm. Color — pink to light red. Position — irregular.

F. Winter hardiness: Need protection outdoors in severe climates.

I claim:

1. A new and distinct variety of rose plant of the miniature rose class, substantially as shown and described, characterized particularly by a plant suitable for growing in pots and outdoor in gardens and by attractive red flowers which are long lasting on the plant.

* * * * *

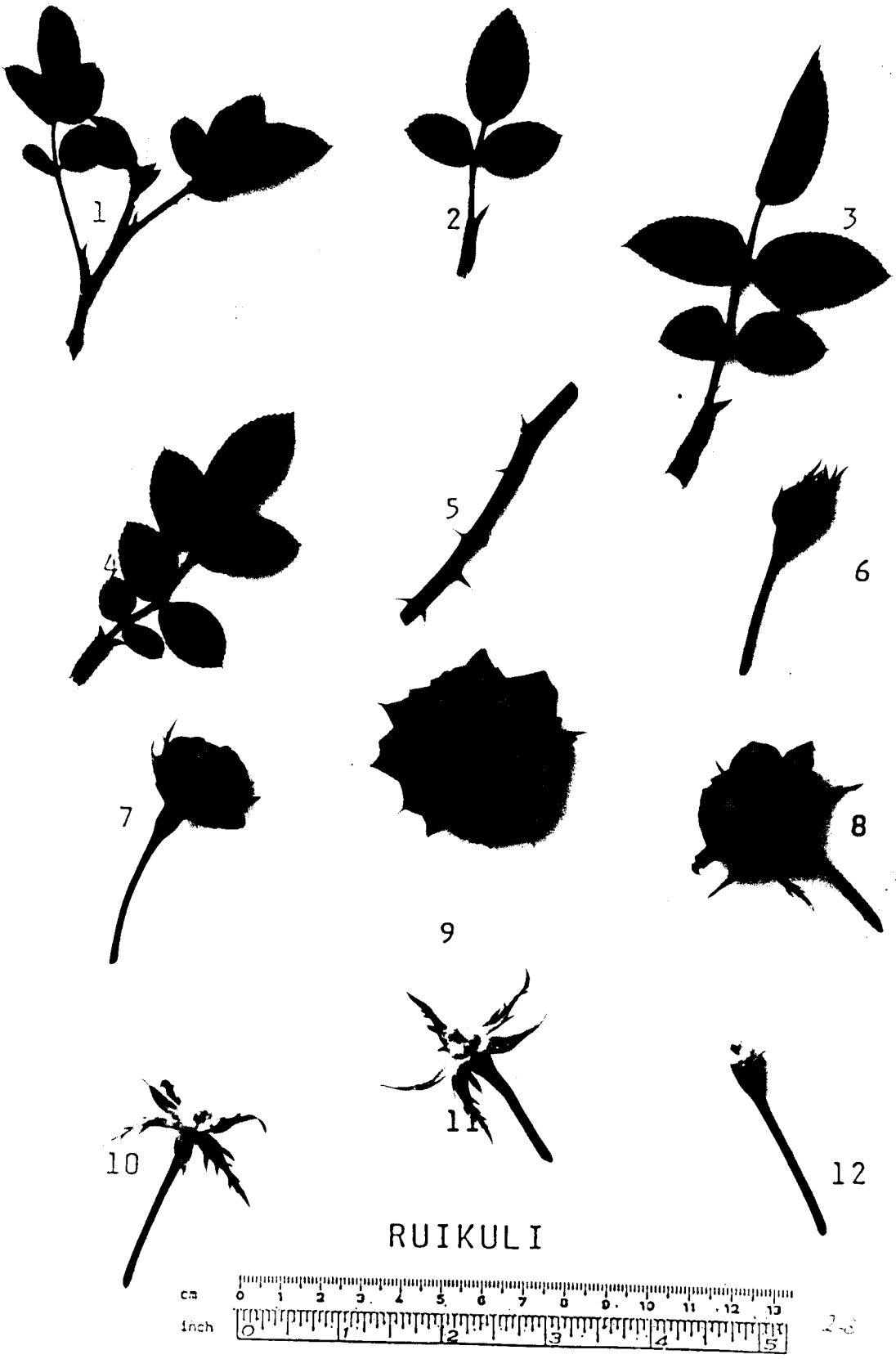
1
2
3
4
5
6
7
8
9
10
11
12
RUIKULI
cm
inch

UNITED STATES PATENT AND TRADEMARK OFFICE

CERTIFICATE OF CORRECTION

PATENT NO. : Plant 7,461

DATED : March 5, 1991

INVENTOR(S) : Kurt Lindberg

It is certified that error appears in the above-identified patent and that said Letters Patent is hereby corrected as shown below:

Column 1, line 5, change "mutataion" to -- mutation --.
Column 1, line 9, change "variety" to -- varietal --.
Column 1, line 39, change "guidelies" to -- guidelines --.
Column 1, line 48, before "young" insert -- a --.

Column 2, line 1, after "stem" insert a comma.
Column 2, line 10, before "FLOWER" insert -- 1. --.
Column 2, line 41, change "petal's" to -- petals' --.

Column 3, line 12, before "REPRODUCTIVE ORGANS" insert -- 2. --.
Column 3, line 23, before "PLANT" insert -- 3. --.

Column 4, line 12, before "Wood:" insert -- D. --.
Column 4, line 14, before "PRICKLES" insert -- E. --.
Column 4, line 23, change "Need" to -- Needs --.

Signed and Sealed this

Twenty-ninth Day of December, 1992

*Attest:*

DOUGLAS B. COMER

*Attesting Officer*

*Acting Commissioner of Patents and Trademarks*